United States Patent
Perrotta et al.

(10) Patent No.: US 7,015,196 B1
(45) Date of Patent: Mar. 21, 2006

(54) BASIC MONOCYCLIC COMPOUNDS HAVING NK2 ANTAGONIST ACTION, PROCESSES FOR THEIR PREPARATION, AND FORMULATIONS CONTAINING THEM

(75) Inventors: Enzo Perrotta, Florence (IT); Danilo Giannotti, Altopascio (IT); Maria Altamura, Florence (IT); Sandro Giuliani, Bagno A Ripoli (IT); Carlo Alberto Maggi, Florence (IT)

(73) Assignee: Menarini Ricerche S.p.A., Pomezia (IT)

( * ) Notice: Subject to any disclaimer, the term of this patent is extended or adjusted under 35 U.S.C. 154(b) by 461 days.

(21) Appl. No.: 10/111,430

(22) PCT Filed: Oct. 17, 2000

(86) PCT No.: PCT/EP00/10181

§ 371 (c)(1),
(2), (4) Date: Sep. 10, 2002

(87) PCT Pub. No.: WO01/29066

PCT Pub. Date: Apr. 26, 2001

(30) Foreign Application Priority Data

Oct. 21, 1999 (IT) ................................ FI99A0217

(51) Int. Cl.
 *A61K 38/12* (2006.01)
 *C07K 7/64* (2006.01)
(52) U.S. Cl. .......................... 514/11; 514/18; 514/217; 530/317; 530/330
(58) Field of Classification Search .................... 514/2, 514/11, 217, 18; 530/317, 330
See application file for complete search history.

(56) References Cited

FOREIGN PATENT DOCUMENTS

| EP | 033174 | 9/1989 |
|---|---|---|
| WO | WO9303059 | 2/1993 |
| WO | WO9321227 | 10/1993 |
| WO | WO9717362 | 5/1997 |
| WO | WO9834949 | 8/1998 |
| WO | WO0008046 | 2/2000 |

OTHER PUBLICATIONS

Kudiacz et al., "Tachykinin-mediated Respiratory Effects in Conscious Guinea Pigs: Modulation by NK, and NK, Receptor Agonists", *European Journal of Pharmacology*, 241, pgs. 17-25 (1993).

McKnight et al., "Pharmacological Specificity of Novel, Synthetic, Cyclic Peptides as Antagonists at Tachykinin Receptors", *J. Pharmacol.* 104, 355-360 (1991).

Quartara et al., "Influence of Lipophilicity on the Biological Activity of Cyclic Pseudopeptide NK-2 Receptor Antagonist", *Journal of Medicinal Chemistry*, (1994).

Peptides, Chemistry and Biology, Proceedings of the 12th American Peptide Symposium, Jun. 16-21, 1991, Cambridge Mass, Published by Escom (1992).

*Primary Examiner*—Anisha Gupta
(74) *Attorney, Agent, or Firm*—Abelman, Frayne & Schwab

(57) ABSTRACT

Basic monocyclic compounds having general formula (I) useful as NK-2 antagonists are described, processes for their preparation and pharmaceutical compositions containing them are also described.

11 Claims, No Drawings

BASIC MONOCYCLIC COMPOUNDS HAVING NK2 ANTAGONIST ACTION, PROCESSES FOR THEIR PREPARATION, AND FORMULATIONS CONTAINING THEM

This application is a National Stage entry of International Application No. PCT/EP00/10181, filed on Oct. 17, 2000.

SCOPE OF INVENTION

The present invention refers to new compounds having general formula:

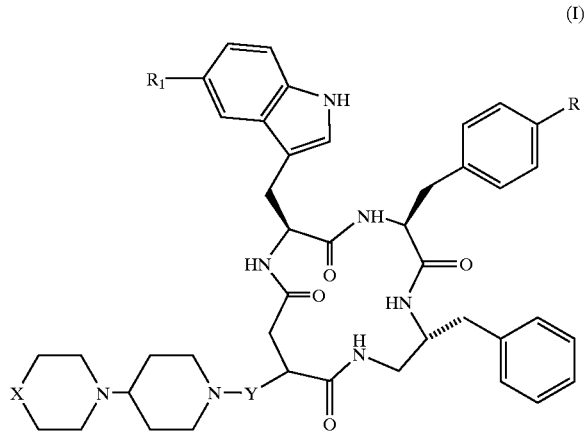

(I)

in which:
X may be $CH_2$, O, S, or SO;
Y is $CH_2$—CO—NH or CO;
R and $R_1$, same or different from one another, represent an H or halogen group, including the respective diastereoisomers and their mixtures, with the proviso that:
when Y is $CH_2$—CO—NH, X is $CH_2$, and R and $R_1$ are H, then the stereochemistry of the carbon atom linked to Y is of the R type.

The presence of free amine groups bestows on the compounds specifically basic characteristics, but included in the present invention are also pharmaceutically acceptable salts of the compounds of general formula (I) with organic and inorganic acids chosen in the group consisting of: hydrochloric acid, hydrobromic acid, sulphuric acid, phosphoric acid, carbonic acid, acetic acid, trifluoroacetic acid, trichloroacetic acid oxalic acid, malonic acid, malic acid, succinic acid, tartaric acid, citric acid, methanesulphonic acid, and p-toluenesulphonic acid.

STATE OF THE ART

The NK2 receptor of tachykinins is widely expressed in the peripheral nervous system of mammals. One of the various effects produced by selective stimulation of the NK2 receptor is the contraction of smooth muscle. Hence, NK2-receptor antagonists may be considered agents that are capable of controlling excessive contraction of the smooth muscle in any pathological condition in which release of tachykinins concurs in the genesis of the corresponding disorder. In particular, the bronchospastic component of asthma, coughing, pulmonary irritations, intestinal spasms or local spasms of the bladder and the ureter during cystitis, renal infections and colics may be considered conditions in which the administration of NK2 antagonists may be effective (E. M. Kudiacz et al., Eur. J. Pharmacol., 1993, 36, 17–25).

Cyclic compounds, in particular cyclic hexapeptides (A. T. McKnight et al., Br. J. Pharmacol., 1991, 104, 355) and bicyclic hexapeptides (V. Pavone et al., WO 93/212227), or cyclic pseudopeptides (L. Quartara et al., J. Med. Chem., 1994, 37, 3630; S. L. Harbeson et al., Peptides, Chemistry and Biology. Proceedings of the Twelfth American Peptide Symposium, 1992, 124) are known in the literature for their high antagonistic activity towards the NK2 receptor of tachykinins.

Recently it has been demonstrated in WO 9834949 that monocyclic products having a lower molecular weight and containing only four bifunctional residues bound together with a peptide or pseudopeptide bond present a pharmacological activity equal to or higher than that of known compounds; they are moreover endowed with considerable selectivity in regard to the human NK2 receptor and are consequently proposed as valid alternatives.

In the compounds according to the present invention, the presence in the products claimed of a grouping of Formula (II)

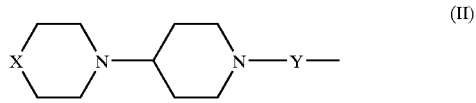

(II)

bestows on the compounds of Formula (I) a surprising activity towards the NK2 receptor when compared to the closest compounds, namely those described in WO 9834949.

DETAILED DESCRIPTION OF THE INVENTION

The purpose of the present invention is therefore to make available new monocyclic compounds containing four residues bound together with a peptide bond and having an antagonistic action on the NK2 receptor, of general formula (I) as previously defined.

Forming part of the present invention are also the pharmaceutically acceptable salts, the processes for their preparation and the pharmaceutical compositions containing them.

More specifically, the halogen group defined for the substituents R and $R_1$ may be chosen from among fluorine, chlorine, bromine, and iodine.

Preferred compounds of the invention are the compounds of general formula (I) in which:
R and $R_1$, same or different from one another, are chosen in the group consisting of H or F, and the other substituents are as defined above.

The following constitute a group of particularly preferred compounds:
1) cyclo{-Suc[1-(R)-2(1,4')-bipiperidinyl-1'-yl-acetyl amino]-Trp-Phe-[(R)—NH—CH($CH_2$—$C_6H_5$)—$CH_2NH$]-}(R=H; $R_1$=H; Y=$CH_2$CONH; X=$CH_2$)
2) cyclo{-Suc[1-(R)-2(4-morpholin-4-yl-piperidin-1-yl)-acetyl amino]-Trp-Phe-[(R)—NH—CH($CH_2$—$C_6H_5$)—$CH_2NH$]-}(R=H; $R_1$=H; Y=$CH_2$CONH; X=O)
3) cyclo{-Suc[1-(R)-2(1,4')-bipiperidinyl-1'-yl-acetyl amino]-Trp-Phe-(4-F)-[(R)—NH—CH($CH_2$—$C_6H_5$)—$CH_2NH$]—} (R=F; $R_1$=H; Y=$CH_2$CONH; X=$CH_2$)
4) cyclo{-Suc[1-(R)-2(4-morpholinyl-4-piperidinyl-1-yl-acetyl) amino]-Trp-(5-F)-Phe-[(R)—NH—CH($CH_2$—$C_6H_5$)—$CH_2NH$]-}(R=H; $R_1$=F; Y=$CH_2$CONH; X=O)

5) cyclo{-Suc[1-(R)-2(4-(1-oxo-1-thiomorpholin-4-piperidin-1-yl)-acetyl amino]-Trp-Phe-[(R)—NH—CH(CH$_2$—C$_6$H$_5$)—CH$_2$NH]-}(R=H; R$_1$=H; Y=CH$_2$CONH; X=SO)

6) cyclo{-Suc[1-(R)-2(4-(1-thiomorpholin-4-yl-piperidin-1-yl)-acetyl amino]-Trp-Phe-[(R)—NH—CH(CH$_2$—C$_6$H$_5$)—CH$_2$NH]—} (R=H; R$_1$=H; Y=CH$_2$CONH; X=S)

7) cyclo{-Suc[1-(1,4')-bipiperidinyl-1'-carbonyl]-Trp-Phe-[(R)—NH—CH(CH$_2$—C$_6$H$_5$)—CH$_2$NH]—} (slow-moving) (R=H; R$_1$=H; Y=CO; X=CH$_2$)

8) cyclo{-Suc[1-(1,4')-bipiperidinyl-1'-carbonyl]-Trp-Phe-[(R)—NH—CH(CH$_2$—C$_6$H$_5$)—CH$_2$NH]—} (fast-moving) (R=H; R$_1$=H; Y=CO; X=CH$_2$).

Pharmaceutically acceptable salts of compounds of Formula (I) include salts with inorganic acids (such as hydrochloric acid, hydrobromic acid, carbonic acid, sulphuric acid, and phosphoric acid) and organic acids (such as acetic acid, trifluoroacetic acid, trichloro-acetic acid, oxalic acid, malonic acid, malic acid, succinic acid, tartaric acid, citric acid, methanesulphonic acid, and p-toluenesulphonic acid).

According to the invention, the compounds of Formula (I) containing peptide or pseudopeptide bonds may be obtained by condensation using techniques that are known in the literature.

As may be seen from Formula (I), for each compound two diastereoisomers are possible (the carbon atom to which the Y group is bound being quaternary). Consequently, the invention refers to the different diastereoisomers of Formula (I) and their mixtures, apart from the case expressly excluded.

The products according to the present invention may be prepared applying the synthesis described in WO 9834949 (see also the literature quoted therein) according to which the monocyclic is obtained by condensing, according to techniques that are known in the chemistry of peptides, firstly the two amino-acid residues, and then by adding the diamine system and the dicarboxylic system, and finally by cyclization.

As a possible alternative to the above synthesis, the products of the present invention may be prepared starting from the diamine system of (R)-1-benzyl-2-(N-benzyloxycarbonylamino)-ethyl amine, to which, according to methodologies known in the chemistry of peptides, Phe, Trp (possibly substituted, respectively by an R group and an R$_1$ group, in which said groups have the meanings previously defined) and a dicarboxylic system (a derivative of succinic acid) are combined. The linear product obtained is cyclized to obtain the desired monocyclic system having general formula (III)

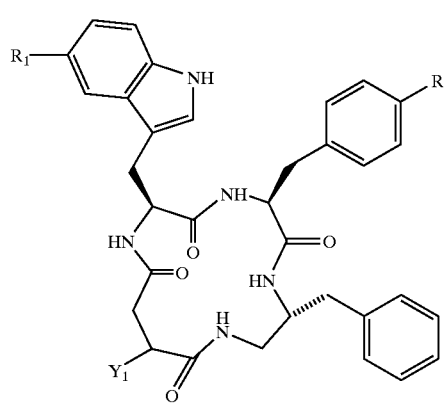

(III)

in which Y$_1$ may be —NH$_2$ or —COOH, and R and R$_1$ have the meanings described above.

The compounds of Formula (III) are then combined with the compounds of Formula (IV)

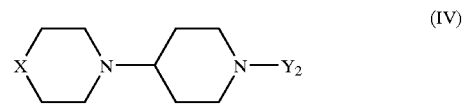

(IV)

in which Y$_2$ may be H or CH$_2$—COOH, and X has the meaning previously defined, to obtain the final compounds of Formula (I).

The compounds of Formula (I) as specified above have been found to be powerful antagonists of the NK2 receptor of tachykinins, and consequently can be administered as agents capable of controlling the excessive contraction of smooth muscle in any pathological condition in which release of tachykinins concurs in the genesis of the corresponding disorder.

In particular, the bronchospastic component of asthma, coughing, pulmonary irritations, intestinal spasms or local spasms of the bladder and the ureter during cystitis, renal infections and colics may be considered conditions in which the administration of the compounds of Formula (I), as NK2 antagonists, may be effective.

The compounds of Formula (I) that form the subject of the present invention or their pharmaceutically acceptable salts are suitable for administration for therapeutic purposes to the higher animals and to man through the parenteral, oral, inhalational, or sublingual routes, achieving pharmacological effects in accordance with the properties described above. For parenteral (intravenous, intramuscular, and intracutaneous) administration, sterile solutions or lyophilized preparations are used. For nasal instillation and for inhalational and sublingual administration, aqueous solutions, aerosol preparations, powders or capsules are used as required.

The doses of active principle in the above-mentioned compositions may be such to allow the delivery of between 0.1 and 10 mg per kg of body weight.

The following are non-limiting examples of the present invention:

EXAMPLE 1 cyclo{-Suc[1-(R)-2(1,4')-bipiperidinyl-1'-yl-acetyl amino]-Trp-Phe-[(R)—NH—CH(CH$_2$—C$_6$H$_5$)—CH$_2$NH]-}

(a compound of general formula (I) in which R=H, R$_1$=H, Y=CH$_2$CONH, X=CH$_2$, and in which C—Y has R configuration).

Used as a starting product is the compound cyclo{-Suc[1-(R)-amino]-Trp-Phe-[(R)—NH—CH(CH$_2$—C$_6$H$_5$)—CH$_2$NH]-}, referred to as Compound A (compound of Formula (III) in which R=H, R$_1$=H, Y$_1$=NH$_2$, and in which the C—Y$_1$ carbon has R configuration), prepared as follows:

a) Synthesis of (R)-1-benzyl-2(N-benzyloxycarbonylamino) ethyl amine (R-1-benzyl-1-(N-tert-butyloxycarbonylamino)ethyl amine, obtained as described in G. Kokotos et-al., J. Chem.

Research (S), 1992, 391, was converted into the corresponding (R)-1-benzyl-1-(N-tert-butyloxycarbonylamino)-2(benzyloxycarbonylamino)ethyl amine, and the latter into (R)-1-benzyl-2-(N-benzyloxycarbonylamino)ethyl amine according to the customary methods of protection and de-protection of amino acids.

b) Synthesis of
Boc-Phe-[(R)—NH—CH(CH$_2$—C$_6$H$_5$)—CH$_2$—NH-Z]

To a solution of Boc-Phe-OH (5.1 g) in 200 ml of anhydrous THF at 5° C. were added in order HOBt (4.2 g), EDC.HCl (4.5 g), and finally, drop by drop, a solution of (R)-1-benzyl-2-(N-benzyloxycarbonylamino)ethyl amine (5.5 g) in 30 ml of anhydrous THF. The solution was left overnight under stirring at room temperature. The solvent was evaporated, and the residue was treated with a 5% aqueous solution of KHSO$_4$. The resulting solid was filtered, washed with water, then with a 10% aqueous solution of NaHCO$_3$, and finally with a saturated solution of NaCl up to pH 7. After vacuum drying, 7.2 grams of a colourless solid product were obtained.

MS (ES$^+$): [MH$^+$]=532; HPLC (Method A1): rt=18.8 min c) Synthesis of
H-Phe-[(R)—NH—CH(CH$_2$—C$_6$H$_5$)—CH$_2$—NH-Z]

TFA (25 ml) was added, under stirring at 0° C., to a suspension of the above compound (4.0 g) in CH$_2$Cl$_2$ (25 ml). The reaction mixture was kept under stirring for 2 hours at room temperature, and the disappearance of the precursor was monitored by means of HPLC analysis. The solution was dried, the residue was dissolved in AcOEt (100 ml), and the resulting organic phase was washed with a saturated aqueous solution of K$_2$CO$_3$ (25 ml), then with brine up to pH 7 (4×50 ml), and finally was dried on anhydrous sodium sulphate. By evaporation of the solvent, 3.5 g of a white solid were obtained.

d) Synthesis of
Boc-Trp-Phe[(R)—NH—CH(CH$_2$—C$_6$H$_5$)—CH$_2$—NH-Z]

HOBT (3.0 g) and EDC.HCl (1.5 g) were added to a solution of Boc-Trp-OH (2.2 g) in THF (100 ml). After stirring for 15 minutes, a solution of H-Phe[(R)—NH—CH(CH$_2$—C$_6$H$_5$)—CH$_2$—NH-Z] (3.1 g) in THF (15 ml) was added. The mixture was left under stirring at room temperature overnight; then the solvent was evaporated, and the residue was treated with a 5% aqueous solution of KHSO$_4$ (100 ml) to obtain a white solid. The solid was filtered and washed again with a 5% aqueous solution of KHSO$_4$ (2×100 ml), then with a 5% aqueous solution of NaHCO$_3$ (3×50 ml), and finally with water (3×50 ml), and was then vacuum dried to obtain 4.9 grams of a white solid.

HPLC (Method A3): rt=18.0 min; MS (TS$^+$): [MH$^+$]=718 e) Synthesis of
H-Trp-Phe[(R)—NH—CH(CH$_2$—C$_6$H$_5$)—CH$_2$—NH-Z]

TFA (15 ml) was added, under stirring at 0° C., to a suspension of the previous compound (1.0 g) in CH$_2$Cl$_2$ (25 ml). The reaction mixture was kept under stirring for 30 minutes at 0° C. and for 2 hours at room temperature, and the disappearance of the precursor was monitored by means of HPLC analysis. After evaporation of the solvent, the residue was diluted with AcOEt (100 ml), washed with a 5% aqueous solution of NaHCO$_3$ (2×30 ml) and brine (30 ml).

The organic phase was dried with MgSO$_4$ and vacuum evaporated at 30° C. to obtain 650 mg of the desired compound.

f) Synthesis of Boc-(D)-Asp{Trp-Phe[(R)—NH—CH(CH$_2$—C$_6$H$_5$)—CH$_2$—NH-Z]}-OBzl To a solution of Boc-(D)-Asp-OBzl (690 mg), HOBt (850 mg), and EDCl.HCl (450 mg) in anhydrous DMF (50 ml) was added, under stirring at room temperature and under nitrogen, a solution of the compound of Example 1(e) (1.3 g). The reaction mixture was left under stirring at room temperature for four hours. After evaporation of the solvent in vacuum conditions, the residue was treated with a 5% aqueous solution of KHSO$_4$ to obtain a solid which was filtered, washed with a 5% aqueous solution of NaHCO$_3$, with water, and dried. The product was crystallized using ethanol to obtain 850 mg of the desired compound as a white solid.

MS (ES$^+$): [MH$^+$]=923; HPLC (Method A1): rt=21.1 min g) Synthesis of Boc-(D)-Asp{(Trp-Phe[(R)—NH—CH(CH$_2$—C$_6$H$_5$)—CH$_2$—NH$_2$]-}—OH The compound of Example 1(f) (800 mg) was solubilized in DMF (10 ml) and diluted with MeOH (40 ml), then hydrogenated in the presence of 10% Pd/C (100 mg) at atmospheric pressure and room temperature for 5 hours. The catalyst was filtered and washed with MeOH. After evaporation of the solvent, 500 mg were obtained of the desired compound as a white solid.

MS (ES$^+$): [MH$^+$]=699; HPLC (Method A2): rt=10.4 min h) Synthesis of cyclo{-Suc[1 (R)NHBoc]-Trp-Phe[(R)—NH—CH(CH$_2$—C$_6$H$_5$)—CH$_2$—NH]-}

To a solution of the compound of Example 1(h) (800 mg) in anhydrous DMF (200 ml) were added, under stirring and in a nitrogen atmosphere, 465 mg of HOBt and 224 mg of EDCl.HCl. The reaction mixture was left under stirring for 5 hours and then, after evaporation of the solvent, the residue was dissolved in ethyl acetate, and the organic phase was washed with a 5% aqueous solution of KHSO$_4$, with a 5% aqueous solution of NaHCO$_3$, and finally with brine, then was dried and evaporated, and the yellow solid obtained (600 mg) was crystallized using 1:1 isopropanol/water to obtain 450 mg of a white solid.

MS (ES$^+$): [MH$^+$]=681; HPLC (Method A2): rt=14.7 min i) Synthesis of cyclo{-Suc[1(R)NH$_2$]-Trp-Phe[(R)—NH—CH(CH$_2$—C$_6$H$_5$)—CH$_2$—NH]-}Compound A TFA (13 ml) was added, under stirring at 0° C., to a suspension of the compound of Example 1 (h) (400 mg) in CH$_2$Cl$_2$ (40 ml). The reaction was conducted for 2 hours at 0° C. and for 2 hours at room temperature. The solvent was evaporated, the residue was treated with NaHCO$_3$ and water, and extracted in ethyl acetate. The organic phase was washed with brine, dried and evaporated to obtain 320 mg of a solid compound.

MS (ES$^+$): [MH$^+$]=581; HPLC (Method A2): rt=12.4 min

A 20-mg sample was purified in an preparative HPLC to obtain 15 mg of trifluoroacetate: cyclo{-Suc[1 (S)NH$_2$]-Trp-Phe[(R)—NH—CH(CH$_2$—C$_6$H$_5$)—CH$_2$—NH]-}.TFA MS (ES⁺): (m/z) [MH⁺]=581; HPLC (Method A2): rt=12.4 min; 1H-NMR 500 MHz (DMSO): d 2.21 (dd, J=6.1, 14.3 Hz, 1H), 2.68–2.82 (m, 5H), 2.95 (dd, J=3.0, 14.4 Hz, 1H), 3.08 (bd, J=12.0 Hz, 1H), 3.38 (dd, J=3.8, 14.2 Hz, 1H), 3.48–5.36 (m, 2H), 3.98–4.08 (m, 1H), 4.11–4.17 (m, 1H), 4.20–4.28 (m, 1H), 6.71 (d, J=9.1 Hz, 1H), 6.98 (t, J=9.1 Hz, 1H), 7.04–7.09 (m, 2H), 7.15–7.21 (m, 4H), 7.21–7.30 (m, 6H), 7.33 (d, J=8.1 Hz, 1H), 7.42 (d, J=7.8 Hz), 7.67 (bs, 1H), 7.82 (bs, 1H), 8.63 (d, J=5.2 Hz, 1H), 10.81 (d, J=1.3 Hz, 1H)

j) Synthesis of 1-(4-piperidinyl)-piperidine acetic acid hydrochloride

A solution of benzylbromo acetate (6.2 ml) in DMSO (30 ml) was added, drop by drop, to a solution of 4-piperidinyl piperidine (5.0 g, titre 90%) in DMSO (50 ml) and DIPEA (4.6 ml). The mixture was stirred at room temperature for 3 hours and was then diluted with AcOEt (250 ml) and washed with water (200 ml), with a 5% aqueous solution of NaHCO₃ (3×100 ml), and with brine (2×100 ml). The pooled aqueous phases were again extracted using AcOEt (2×50 ml), and the pooled organic phases were dried on anhydrous sodium sulphate and evaporated to yield an orange-coloured oil, which was treated with ethyl ether (200 ml) and precipitated by addition, at 0° C., of HCl 4N in dioxane (11 ml) to obtain 7.0 g of an orange solid.

The solid was solubilized in methanol (230 ml) in the presence of a 10% Pd/C catalyst (0.5 g) and was hydrogenated at room pressure for 5 hours until complete disappearance of the reagent (control via TLC: EtOAc/i-PrOH/TEA, 80/17/3).

The reaction mixture was filtered, and the solution was dried to obtain an oil that was solidified by treatment with ethyl acetate, washed with ethyl ether, and vacuum dried to obtain 4.7 g of a yellowish solid.

MS (ES⁺): [MH⁺]=227 k) HOBt (77 mg) and EDC.HCl (36 mg) were added in order to a suspension of 1-(4-piperidinyl-piperidine acetic acid hydrochloride (50 mg) in DMF (3 ml). The mixture was stirred for ten minutes, and 110 mg of Compound A were added. The clear solution was stirred for 3 hours at room temperature. The solution was dry-evaporated, and the residue was treated with acetonitrile (1 ml) and dry evaporated again. The resulting crude product was treated with AcOEt until an ivory-coloured solid (80 mg) was obtained, which was purified on preparative HPLC using the method P1 to obtain 25 mg of the final product.

MS (ES⁺): [MH⁺]=789.5; HPLC (Method A2): rt=11.2 min

With a similar experimental procedure, the following compounds were obtained:

EXAMPLE 2 cyclo{-Suc[1-(R)-2(4-morpholin-4-yl-piperidin-1-yl)-acetyl amino]-Trp-Phe-[(R)—NH—CH(CH₂—C₆H₅)—CH₂NH]-}

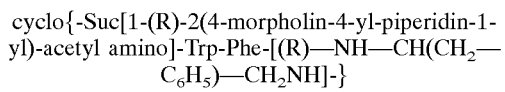

(compound of general formula (I) in which R=H; R₁=H; Y=CH₂CONH; X=O)

a) Synthesis of 1-benzyloxycarbonyl-piperidin-4-one

Triethyl amine (9.2 ml) and N-benzyloxycarbonyl succinimide (9.0 g) were added to a solution of hydrated piperidin-4-one hydrochloride (5.0 g) in THF/H₂O (10/6, 160 ml) cooled to 5° C. The mixture was stirred for 10 minutes at 5° C. and for 2 hours at room temperature.

The organic solvent was evaporated, and the resulting aqueous phase was extracted with AcOEt (3×70 ml). The pooled organic phases were washed with water (70 ml), with HCl 1N (70 ml), with a saturated aqueous solution of NaHCO₃ (3×70 ml), and with brine (70 ml). The organic phase was dried on anhydrous sodium sulphate and, after evaporation of the solvent at reduced pressure, 8.2 g of product as a viscous oil were obtained.

MS (EI⁺): [M⁺]=233; TLC: Rf=0.36 (EtOAc/Hexane, 50/50); HPLC (Method A1): rt=9.5 min b) Synthesis of (4-piperidin-4-yl-morpholin-1-yl)-benzyloxycarbonyl Sodium cyanoborohydride (2.39 g) and glacial acetic acid (2.80 ml) were added to a solution of 1-benzyloxycarbonyl-piperidin-4-one (8.07 g) and morpholine (2.80 ml) in methanol (140 ml), and the mixture was left to react overnight at room temperature. The solvent was evaporated, and the residue was treated with water (70 ml) and acidified with concentrated HCl up to pH 1. The mixture was left under a suction hood until complete destruction of the reagent in excess. The resulting solution was basified by addition of solid K₂CO₃ in small portions and extracted with AcOEt (3×70 ml). The pooled organic phases were dried on anhydrous sodium sulphate and evaporated to yield 5.44 g of product in the form of an oil.

MS (ES⁺): [MH⁺]=305; TLC: Rf=0.57 (EtOAc/MeOH/TEA, 85/14/1); HPLC (Method A2): rt=8.0 min c) Synthesis 4-piperidin-4-yl-morpholin bis hydrochloride Concentrated HCl (2.50 ml) was added to a solution of (4-piperidin-4-yl-morpholin-1-yl)-benzyloxycarbonyl (5.44 g) in methanol (150 ml), and the resulting mixture was hydrogenated at room pressure in the presence of 10% Pd/C (0.33 g) for 10 hours. The reaction mixture was filtered and washed repeatedly with methanol. The eluate was pooled and evaporated at reduced pressure. The resulting solid was washed with ethyl ether, filtered and vacuum dried to obtain 3.34 g of product.

MS (ES⁺): [MH⁺]=171 d) Synthesis of 2-(4-morpholin-4-yl-piperidin-1-yl) acetic acid

The product was obtained according to the procedure described in point j) of Example 1, using 4-piperidin-4-yl-morpholine instead of piperidinyl piperidine.

e) To a solution of 2-(4-morpholin-4-yl-piperidin-1-yl) acetic acid (19 mg) in DMF (5 ml) were added HOBt (9.4 mg) and EDC.HCl (35.2 mg). After stirring for 15 minutes at room temperature, a solution of Compound A (50 mg) in DMF (5 ml) was added. The pH of the solution was corrected from pH 4 to pH 6 by addition of triethyl amine. The mixture was stirred overnight and the solvent was vacuum evaporated. The resulting residue was purified on a preparative HPLC (Method P2) to obtain 35 mg of product.

MS (ES⁺): [MH⁺]=791.5; HPLC (Method A2): rt=10.9 min

EXAMPLE 3 cyclo{-Suc[1-(R)-2(1,4')-bipiperidinyl-1'-yl-acetyl amino]-Trp-Phe-(4-F)-[(R)—NH—CH(CH$_2$—C$_6$H$_5$)—CH$_2$NH]-}

(compound of general formula (I) in which R=F; R$_1$=H; X=CH$_2$; Y=CH$_2$CONH) The compound was obtained using the procedure described in Example 1(a)–(k), but using Boc-Phe-(4-F)—OH instead of Boc-Phe-OH.

MS (ES$^+$): [MH$^+$]=807.4; HPLC (Method A2): rt=11.4 min

EXAMPLE 4 cyclo{-Suc[1-(R)-2(4-morpholinyl-4-piperidinyl-1-yl-acetyl) amino]-Trp-(5-F)-Phe-[(R)-N H—CH(CH$_2$—C$_6$H$_5$)—CH$_2$NH]-}

(compound of general formula (I) in which R=H; R$_1$=F; X=O; Y=CH$_2$CONH)

The compound was obtained using the procedure described in Example 2(a)–2(e) but using Boc-Trp-(5-F)—OH instead of Boc-Trp-OH.

MS (ES$^+$): [MH$^+$]=809.7; HPLC (Method A2): rt=11.5 min

EXAMPLE 5 cyclo{-Suc[1-(R)-2(4-(1-oxo-1-thiomorpholin-4-yl)-piperidin-1-yl)acetyl amino]-Trp-Phe-[(R)—NH—CH(CH$_2$—C$_6$H$_5$)—CH$_2$NH]-}

(compound of general formula (I) in which R=H; R$_1$=H; Y=CH$_2$CONH; X=SO)

a) Synthesis of 1-tert-butoxycarbonyl-4-(1-thiomorpholin-4-yl)piperidine

To a solution of 1-tert-butoxycarbonyl-piperidin-4-one (2.0 g) in methanol (45 ml) were added thiomorpholin (1 ml), acetic acid (1.2 ml), and finally NaCNBH$_3$ (630 mg). The mixture was left to react overnight. The mixture was concentrated to a is small volume, diluted with water (30 ml) and HCl 1N to pH 1.5, and extracted with ethyl acetate (3×20 ml). The pooled organic phases were washed with a 5% aqueous solution of NaHCO$_3$ and brine, and dried on anhydrous sodium sulphate. The solid was evaporated, and the resulting oil was purified on a chromatographic column, eluating with 95:5 ethyl acetate/methanol to obtain 1.4 g of product in the form of a colourless oil.

MS (ES$^+$): [MH$^+$]=287; TLC: rf=0.58 (EtOAc/MeOH, 95/5, iodine detector)

b) Synthesis of 1-oxo-1 thiomorpholin-4-yl-piperidine

To a solution of (4-(1-thiomorpholin-4-yl-piperidin-1-yl)-tert-butoxycarbonyl (1.0 g) in methylene chloride (40 ml) and trifluoroacetic acid (0.3 ml) cooled to −15° C. was added, drop by drop, a solution of meta-chloroperbenzoic acid (70%, 0.9 g) in methylene chloride (40 ml). When the addition was completed, the mixture was left to react for 30 minutes at 0° C. and was diluted with dichloromethane until a homogeneous mixture was obtained. The reaction mixture was transferred into a separating funnel and washed repeatedly with a 5% aqueous solution of NaHCO$_3$ and brine, and was then dried on anhydrous magnesium sulphate. An oil was obtained by evaporation of the solvent.

c) The product previously obtained was solubilized in a 2:1 mixture of methylene chloride and trifluoroacetic acid (60 ml) cooled to 5° C. The solution was left to react for 1 hour at 5° C. and for 2 hours at room temperature. The reaction mixture was doubled in volume by addition of toluene, and was then vacuum evaporated until a dense oil was obtained consisting of the product in the form of trifluoroacetic salt. The amount of product obtained was 0.9 grams.

MS (ES$^+$): [MH$^+$]=203 d) Synthesis of 2 (4-(1-oxo-1-thiomorpholin-4-yl)-piperidin-1-yl-acetyl-tert-butyl ester To a solution of 1-oxo-1-thiomorpholin-4-piperidine (0.9 g) in DMSO (8 ml) were added DIPEA (0.7 ml), and then tert-butyl-bromo acetate (0.6 ml), and the mixture was left to react overnight at room temperature. The formation of the product of reaction was revealed by TLC (chloroform/methanol 9/1, iodine detector, Rf=0.4). The reaction mixture was diluted with ethyl acetate and washed with a 5% aqueous solution of NaHCO$_3$ and brine, and dried on anhydrous sodium sulphate. The solvent was evaporated, and 0.75 g of a solid was obtained, which was sufficiently pure to be used as it was.

MS (ES$^+$): [MH$^+$]=317 e) Synthesis of 2(4-(1-oxo-1-thiomorpholin-4-yl)-piperidin-1-yl)-acetic acid To a solution of 2(4-(1-oxo-1-thiomorpholin-4-yl)-piperi-din-1-yl-acetyl tert-butyl ester (200 mg) in dichloromethane (4 ml) was added trifluoroacetic acid (2 ml), and the solution was stirred for 3 hours. The disappearance of the reagent was verified by TLC (AcOEt/MeOH, 9:1), and the solution was diluted with toluene and dry evaporated. The resulting residue was treated with ethyl ether, and the solid that formed was filtered, washed with ether, and dried in a dryer to obtain 100 mg of product in the form of trifluoroacetate salt.

MS (ES$^+$): [MH$^+$]=261 f) To a solution of 2(4-(1-oxo-1-thiomorpholin-4-yl)-piperi-din-1-yl) acetic acid of the previous example (50 mg) in DMF (4 ml) were added HOBt (30 mg) and EDC.HCl (30 mg). After stirring for 15 minutes at room temperature, Compound A (50 mg) was added. The pH of the solution was corrected from pH 4 to pH 6 by addition of triethyl amine. The mixture was stirred overnight, and the solvent was vacuum evaporated. The resulting residue was purified on preparative HPLC (Method P2) to obtain 24 mg of product.

MS (ES$^+$): [MH$^+$]=824; HPLC (Method A2): rt=10.8 min

EXAMPLE 6 cyclo{-Suc[1-(R)-2(4-(1-thiomorpholin-4-yl)-piperi-din-1-yl)-acetyl amino]-Trp-Phe-[(R)—NH—CH(CH$_2$—C$_6$H$_5$)—CH$_2$NH]-}

(Compound of general formula (I) in which R=H; R$_1$=H; Y=CH$_2$CONH; X=S)

The compound was obtained using the procedure described in Example 5, excluding the intermediate step 5(b).

MS (ES$^+$): [MH$^+$]=808; HPLC (Method A2): rt=12.9 min

EXAMPLE 7 cyclo{-Suc[1-(R or S)-(1,4')-bipiperidinyl-1'-carbonyl]-Trp-Phe[(R)—NH—CH(CH$_2$—C$_6$H$_5$)—CH$_2$NH]-}slow-moving (Compound of general formula (I) in which R=H; R$_1$=H; X=CH$_2$; Y=CO)

a) Synthesis of Boc-Trp-Phe[(R)—NH—CH(CH$_2$—C$_6$H$_5$)—CH$_2$NH$_2$]

To a solution of Boc-Trp-Phe[(R)—NH—CH(CH$_2$—C$_6$H$_5$)—CH$_2$NH-Z] (1.20 g) in methanol (36 ml) and DMF (14 ml) was added 10% Pd/C (120 mg). The mixture underwent stirring and was hydrogenated at room temperature and atmospheric pressure for 2 hours. The mixture was filtered, and the solid was washed with methanol. The eluates were pooled and evaporated until a viscous oil was obtained, which was solubilized in ethyl acetate. The resulting solution was washed with water and brine, and was dried on anhydrous sodium sulphate. By evaporation of the organic phase, 870 mg of a white solid were obtained.

MS (ES$^+$): [MH$^+$]=584; HPLC (Method A3): rt=11.8 min b) Synthesis of Boc-Trp-Phe{(R)—NH—CH(CH$_2$—C$_6$H$_5$)—CH$_2$NH-[2-(4-nitrobenzyloxycarbonyl)-4-tert-butyl)-succin-1-yl]}

To a solution of 2-(4-nitro-benzyloxycarbonyl)-succinic acid 4-tert-butyl ester (424 mg) in DMF (20 ml) at 0° C. were added HOBt (490 mg), EDCl.HCl (250 mg), and finally Boc-Trp-Phe[(R)—NH—CH(CH$_2$—C$_6$H$_5$)—CH$_2$NH$_2$] (700 mg). The mixture was made to react for 2 hours at room temperature. The solvent was removed by vacuum evaporation, and the resulting residue was treated with a 5% aqueous solution of KHSO$_4$ to obtain a solid, which was filtered, washed with a 5% aqueous solution of NaHCO$_3$, and with water, and was finally vacuum dried on CaCl$_2$ to obtain 1.05 g of a solid.

MS (ES$^+$): [MH$^+$]=919; HPLC (Method A4): rt=20.3 min c) Synthesis of cyclo{Suc[1-(4-nitro-benzyloxycarbonyl)]-Trp-Phe-[(R)—NH—CH(CH$_2$—C$_6$H$_5$)—CH$_2$NH]-}

To 20 ml of TFA cooled to 0° C. was added, in small portions, 1.0 g of Boc-Trp-Phe{(R—NH—CH(CH$_2$—C$_6$H$_5$)—CH$_2$NH-[2-(4-nitro-benzyloxycarbonyl)-4-tert-butyl)-succin-1-yl]}. The mixture, left to react for 30 minutes at 0° C., was vacuum concentrated and diluted with DMF, and then was evaporated again until an oil was obtained that was treated with ethyl ether to yield a solid. The solid was filtered and washed with ethyl ether until an amorphous yellow solid was obtained, consisting of H-Trp-Phe{(R)—NH—CH(CH$_2$—C$_6$H$_5$)—CH$_2$NH-[2-(4-nitro-benzyloxycarbonyl)]}-1-succinic acid; 710 mg of product were obtained.

PyBOP (160 mg) and TEA (108 µl) were added to a 200-mg solution of H-Trp-Phe{(R)—NH—CH(CH$_2$—C$_6$H$_5$)—CH$_2$NH-[2-(4-nitro-benzyloxycarbonyl)]}-1-succinic acid in DMF (10 ml) under nitrogen at 0° C. The solution underwent stirring at room temperature for hours and was monitored using HPLC. The reaction mixture was dried, and the residue was dissolved in ethyl acetate. The organic phase was washed with a 5% aqueous solution of KHSO$_4$, with a 5% aqueous solution of NaHCO$_3$, and with brine, and was finally dehydrated on anhydrous sodium sulphate. After filtration and evaporation of the solvent, a residue was obtained weighing 180 mg and consisting of the product as a mixture of diastereoisomers in position 1-succinyl. The two diastereoisomers are defined as "fast-moving" (fm) and "slow-moving" (sm).

MS (ES$^+$): [MH$^+$](fm)=[MH$^+$](sm)=745; HPLC (Method A3): rt(fm)=15.1 min, rt(sm)=15.6 min d) To the mixture of cyclo{Suc[1-(4-nitro-benzyloxycarbonyl)]-Trp-Phe-[(R)—NH—CH(CH$_2$—C$_6$H$_5$)—CH$_2$NH]-}diastereoisomers (100 mg) was added a 1:1 mixture of water and isopropanol (3 ml) containing K$_2$CO$_3$ (34 mg). The reaction mixture was left to react for 18 hours at room temperature, and was then concentrated, diluted with water, and extracted with ethyl acetate to eliminate the non-reacted product. The aqueous phase was acidified with HCl 1N until a white opalescence was formed, and was extracted again with ethyl acetate. The organic phase of the second extraction was dried on anhydrous sodium sulphate and evaporated to yield 55 mg of a white solid.

The solid was dissolved in DMF (3 ml), and HOBt (50 mg), EDCl.HCl (32 mg), and [1,4]bipiperidine (15 µl) were added in order. After 24 hours under stirring, the reaction mixture was diluted with 3 ml of a mixture consisting of 80:20 water/acetonitrile containing 0.1% TFA, and was purified using preparative HPLC (Method P3) to separate the two diastereoisomer products present. In this way, 30 mg of fast-moving product were obtained as a white solid.

MS (ES$^+$): [MH$^+$]=760.4; HPLC (Method A2): rt=12.6 min

Following a similar experimental procedure, the following compound was obtained:

EXAMPLE 8 cyclo{-Suc[1-(S or R)-(1,4')-bipiperidinyl-1'-carbonyl]-Trp-Phe[(R)—NH—CH(CH$_2$—C$_6$H$_5$)—CH$_2$NH]-}fast-moving (Compound of general formula (I) in which R=H; R$_1$=H; X=CH$_2$; Y=CO)

The compound was separated from the corresponding diastereoisomer by preparative HPLC (Method P3).

MS (ES$^+$): [MH$^+$]=760.4; HPLC (Method A2): rt=13.0 min

Preparative HPLC methods

Mobile phase: A=H$_2$O+0.1% TFA; B=CH$_3$CN+0.1% TFA

Method P1
Column: Symmetry RP18, 7 µm, 100 Å, 19×300 mm
Gradient from A:B=80:20 to A:B=50:50 in 60 min, then from A:B=50:50 to A:B=20:80 in 120 min
Flow rate: 15 ml/min
I=220, 270 nm Method P2
Column: Symmetry RP18, 7 µm, 100 Å, 19×300 mm
Gradient from A:B=80:20 to A:B=20:80 in 120 min
Flow rate: 15 ml/min
I=220, 270 nm Method P3
Column: Vydac RP18, 20 µm, 22×250 mm
Gradient from A:B=80:20 to A:B=20:80 in 120 min
Flow rate: 20 ml/min I=240 nm Analytical HPLC Methods
Mobile phase: A=$H_2O$+0.1% TFA; B=$CH_3CN$+0.1% TFA Method A1
Column: Symmetry C18, 5 mm, 100 Å, 3.9×150 mm
Gradient from A:B=80:20 to A:B=20:80 in 20 min
Flow rate: 1 ml/min
I=215 nm Method A2
Column: Luna 5 μm, C8(2), 100 Å, 4.6×250 mm
Gradient from A:B=80:20 to A:B=20:80 in 20 min
Flow rate: 1 ml/min
I=220, 270 nm Method A3
Column: Symmetry C8 5 mm, 100 Å, 3.9×150 mm
Gradient from A:B=80:20 to A:B=20:80 in 20 min
Flow rate: 1 ml/min
I=220, 270 nm Method A4
Column: Symmetry C8 5 mm, 100 Å, 3.9×150 mm
Gradient from A:B=80:20 to A:B=20:80 in 20 min followed by A:B=20:80 for 6 min
Flow rate: 1 ml/min
I=220, 270 nm Abbreviations: For the nomenclature and abbreviations of the amino acids, reference is made to the recommendations of IUPAC-IUB Joint Commission on Biochemical Nomenclature (Eur. J. Biochem. 1984, 138, 9); the amino acids are understood as being in the S configuration if not otherwise specified. The other abbreviations used are: Bzl=benzyl; DIEA=DIPEA=N,N-diisopropyl ethyl amine; DMF=dimethyl formamide; EDC=EDCl=1-(3-dimethylaminopropyl)3-ethylcarbodiimide; PyBOP=benzotriazol-1-yl-oxy-tris-pyrrolidino-phosphoniohexafluorophosphate; TEA=triethyl amine; TFA=trifluoroacetic acid; Z=Cbz=N-benzyloxycarbonyl; Boc=tert-butoxycarbonyl; -Suc-=succinyl; DMF= N,N-dimethyl formamide; NKA=neurokinin A; HOBt=1-hydroxybenzotriazole; rt=retention time; THF=tetrahydrofuran. The numbering of the substituents on the succinic group designated as -Suc(1-$NH_2$)— is obtained with Y1=$NH_2$.

Biological Activity

The compounds described in the present invention act as antagonists to the NK2 receptor of tachykinins. The biological activity was evaluated in three in vitro functional tests, using rabbit pulmonary artery (RPA), hamster trachea (HT) and rat urinary bladder (RUB), according to the methods described by C. A. Maggi et al., Br. J. Pharmacol., 1990, 100, 588; P. D'Orleans-Juste et al., Eur. J. Pharmacol., 1986, 125, 37; and C. A. Maggi et al., J. Pharmacol. Exp. Ther., 1988, 246, 308. The affinity of the compounds for the human NK2 receptor was evaluated in a binding test using membranes of Chinese hamster ovary (CHO) cells transfected with the NK2 receptor of human ileum and the radioligand [$^{125}$I]NKA (Amersham, non-specific activity 2000 Ci/mmol) at the concentration of 100 pM in competition studies. The substances under examination were tested in a concentration range between 0.01 nM and 10 mM. At the end of incubation (30 min, 20° C.) the test specimens were filtered, and radioactivity was determined using a gamma-counter.

The data emerging from the functional studies were expressed as $pA_2$ (O. Arunlakshana and H. O. Shild, Br. J. Pharmacol. Chemother., 1959, 14, 45), and the data emerging from the binding studies were expressed as pKi (log Ki calculated with the LIGAND program; P. J. Munson et al., Anal. Biochem., 1980, 107, 220).

The compounds of the invention were found to be active in the tests referred to above, with $pA_2$ values of up to 9.8 and pKi values of up to 10.3.

Table of activity

| Compound (example) | pKi | $pA_2$ RPA | HT | RUB |
|---|---|---|---|---|
| WO9834949; Ex. 27 | 8.5 | 7.8 | 8.5 | |
| WO9834949; Ex. 35 | 8.6 | 8.4 | 8.5 | |
| WO9834949; Ex. 36 | 8.7 | 7.9 | | |
| WO9834949; Ex. 37 | 8.8 | | | 8.2 |
| WO9834949; Ex. 46 | 8.1 | 7.7 | 8.3 | 7.7 |
| Example 1 | 9.4 | 8.7 | 8.8 | 9.2 |
| Example 2 | 9.7 | | | 9.8 |
| Example 3 | 9.6 | | | 9.3 |
| Example 4 | 10.1 | | | 9.7 |
| Example 7 | 10.3 | | | 9.1 |
| Example 8 | 9.5 | | | 9.1 |

What is claimed is:

1. Compounds having general formula (I):

in which:
X may be $CH_2$, O, S, or SO;
Y is $CH_2$—CO—NH or CO;
R and $R_1$, same or different from one another, represent an H or halogen group selected from the group consisting of fluorine, chlorine, bromine, and iodine;
including the respective diastereoisomers and their mixtures;
with the proviso that when Y is $CH_2$—CO—NH, X is $CH_2$, and R and $R_1$ are H, then the stereochemistry of the carbon atom linked to Y is of the R type;
and the pharmaceutically acceptable salts of the compounds of general formula (I) with organic and inorganic acids selected from the group consisting of hydrochloric acid, hydrobromic acid, sulphuric acid, phosphoric acid, carbonic acid, acetic acid, trifluoroacetic acid, trichloroacetic acid, oxalic acid, malonic acid, malic acid, succinic acid, tartaric acid, citric acid, methanesulphonic acid, and p-toluenesulphonic acid.

2. Compounds according to claim 1 wherein R and $R_1$ may be the same as or different from one another and are selected from the group consisting of H and F, and the other substituents are as defined above.

3. Compounds according to claim 2, as listed below:
   i) cyclo {-Suc[1-(R)-2(1,4')-bipiperidinyl-1'-yl-acetyl amino]-Trp-Phe-[(R)—NH—CH(CH$_2$—C$_6$H$_5$)—CH$_2$NH]—} (R=H; R$_1$=H; Y=CH$_2$CONH; X=CH$_2$)
   ii) cyclo {-Suc[1-(R)-2(4-morpholin-4-yl-piperidin-1-yl)-acetyl amino]-Trp-Phe-[(R)—NH—CH(CH$_2$—C$_6$H$_5$)—CH$_2$NH]—} (R=H; R$_1$=H; Y=CH$_2$CONH; X=O)
   iii) cyclo {-Suc[1-(R)-2(1,4')-bipiperidinyl-1'-yl-acetyl amino]-Trp-Phe-(4-F)-[(R)—NH—CH(CH$_2$—C$_6$H$_5$)—CH$_2$NH]—} (R=F; R$_1$=H; Y=CH$_2$CONH; X=CH$_2$)
   iv) cyclo {-Suc[1-(R)-2(4-morpholinyl-4-piperidinyl-1-yl-acetyl) amino]-Trp-(5-F)-Phe-[{(R)—NH—CH(CH$_2$—C$_6$H$_5$)—CH$_2$NH]—} (R=H; R$_1$=F; Y=CH$_2$CONH; X=O)
   v) cyclo {-Suc[1-(R)-2(4-(1-oxo-1-thiomorpholin-4-piperidin-1-yl)-acetyl amino]-Trp-Phe-[(R)—NH—CH(CH$_2$—C$_6$H$_5$)—CH$_2$NH]—} (R=H; R$_1$=H; Y=CH$_2$CONH; X=SO)
   vi) cyclo {-Suc[1-(R)-2(4-(1-thiomorpholin-4-yl piperidin-1-yl)-acetyl amino]Trp-Phe-[(R)—NH—CH(CH$_2$—C$_6$H$_5$)—CH$_2$NH]—} (R=H; R$_1$=H; Y=CH$_2$CONH; X=S)
   vii) cyclo {-Suc[1-(1,4')-bipiperidinyl-1'-carbonyl]-Trp-Phe-[(R)—NH—CH(CH$_2$—C$_6$H$_5$)—CH$_2$NH]—} (slow-moving) (R=H; R$_1$=H; Y=CO; X=CH$_2$)
   viii) cyclo {-Suc[1-(1,4')-bipiperidinyl-1'-carbonyl]-Trp-Phe-[(R)—NH—CH(CH$_2$—C$_6$H$_5$)—CH$_2$NH]—} (fast-moving) (R=H; R$_1$=H; Y=CO; X=CH$_2$).

4. Process for the preparation of compounds having general formula I,

I which comprises the following steps:
   i) combining the diamine system represented by (R)-1-benzyl-2-(N-benzyloxycarbonylamino)-ethyl amine with Phe and Trp, possibly substituted, respectively by an R group and an R$_1$ group, in which R and R$_1$ are the same or different from one another and represent an H or halogen group selected from the group consisting of chlorine, bromine, and iodine;
   ii) condensing to the above the dicarboxylic system represented by a derivative of succinic acid, and cyclizing the linear product obtained to yield the desired monocyclic system having general formula (III)

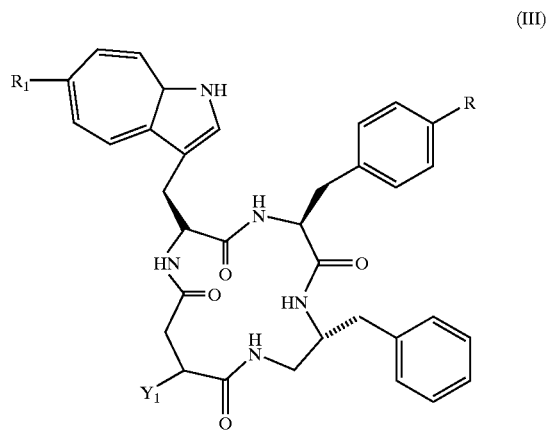

in which Y$_1$ may be —NH$_2$ or —COOH, and R and R$_1$ have the meanings described above;
   iii) finally condensing the compounds of Formula (III) with the compounds of Formula (IV)

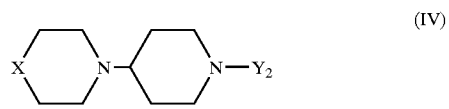

in which Y$_2$ may be H or CH$_2$—COOH, and X has the meaning previously defined, to yield the final compounds of general formula (I).

5. Pharmaceutical compositions containing as active principle compounds having general formula (I) according to claim 1 in combination with pharmaceutically acceptable carriers or excipients.

6. Pharmaceutical compositions according to claim 5 for use as tachykinin antagonists.

7. Pharmaceutical compositions according to claim 6 for use as antagonists towards the human NK2 receptor.

8. Pharmaceutical compositions according to claim 7 for use in the treatment of the bronchospastic component of asthma, coughing, pulmonary irritations, intestinal spasms or local spasms of the bladder and the ureter during cystitis, renal infections and colics.

9. Method for the treatment of the bronchospastic component of asthma, coughing, pulmonary irritations, intestinal spasms or local spasms of the bladder and the ureter during cystitis, renal infections and colics, in which the patient is administered between 0.1 and 10 mg/kg of body weight of active principle consisting of products of Formula (I) according to claim 1.

10. Pharmaceutical compositions containing as active principle compounds having general formula (I) according to claim 2 in combination with pharmaceutically acceptable carriers and excipients.

11. Pharmaceutical compositions containing as active principle compounds having general formula (I) according to claim 3 in combination with pharmaceutically acceptable carriers or excipients.

* * * * *